(12) United States Patent
Zhang et al.

(10) Patent No.: US 9,962,459 B2
(45) Date of Patent: May 8, 2018

(54) ULTRATHIN FLUID-ABSORBENT CORES

(75) Inventors: Xiaomin Zhang, Charlotte, NC (US); Michael A. Mitchell, Waxhaw, NC (US)

(73) Assignee: BASF SE, Ludwigshafen (DE)

( * ) Notice: Subject to any disclaimer, the term of this patent is extended or adjusted under 35 U.S.C. 154(b) by 1618 days.

(21) Appl. No.: 13/172,452

(22) Filed: Jun. 29, 2011

(65) Prior Publication Data

US 2012/0004632 A1   Jan. 5, 2012

Related U.S. Application Data

(60) Provisional application No. 61/360,932, filed on Jul. 2, 2010.

(51) Int. Cl.
*A61L 15/60* (2006.01)
*A61F 13/53* (2006.01)

(52) U.S. Cl.
CPC .............. *A61L 15/60* (2013.01); *A61F 13/53* (2013.01); *A61F 2013/530547* (2013.01); *A61F 2013/530708* (2013.01)

(58) Field of Classification Search
USPC ................. 604/364–370, 372–373; 442/151
See application file for complete search history.

(56) References Cited

U.S. PATENT DOCUMENTS

| | | | |
|---|---|---|---|
| 6,972,011 B2 | 12/2005 | Maeda et al. | |
| 2003/0181115 A1 | 9/2003 | Nagasuna et al. | |
| 2004/0058805 A1* | 3/2004 | Nakajima et al. | 502/152 |
| 2005/0137085 A1 | 6/2005 | Zhang et al. | |
| 2006/0004336 A1 | 1/2006 | Zhang et al. | |
| 2006/0058747 A1* | 3/2006 | Nguyen et al. | 604/368 |
| 2007/0135785 A1 | 6/2007 | Qin et al. | |
| 2007/0156108 A1 | 7/2007 | Becker et al. | |
| 2007/0179464 A1* | 8/2007 | Becker et al. | 604/366 |
| 2008/0125735 A1 | 5/2008 | Busam et al. | |
| 2009/0012488 A1* | 1/2009 | Braig et al. | 604/359 |
| 2010/0247916 A1 | 9/2010 | Hamilton et al. | |

FOREIGN PATENT DOCUMENTS

| | | |
|---|---|---|
| EP | 1293187 A1 | 3/2003 |
| EP | 1447066 A1 | 8/2004 |
| EP | 1447067 A1 | 8/2004 |
| EP | 1609448 A1 | 12/2005 |
| JP | 2004/313580 A | 11/2004 |
| WO | WO-2004071363 A1 | 8/2004 |
| WO | WO-2005097025 A1 | 10/2005 |
| WO | WO-2007/121937 A2 | 11/2007 |
| WO | WO-2008155699 A1 | 12/2008 |
| WO | WO-2008155701 A2 | 12/2008 |
| WO | WO-2008155702 A1 | 12/2008 |
| WO | WO-2008155710 A1 | 12/2008 |
| WO | WO-2008155711 A1 | 12/2008 |
| WO | WO-2008155722 A2 | 12/2008 |
| WO | WO-2010/015591 A1 | 2/2010 |
| WO | WO-2010108875 A1 | 9/2010 |
| WO | WO-2011/117187 A1 | 9/2011 |

OTHER PUBLICATIONS

Buchholz, Fredric L., et al.. *Modern Superabsorbent Polymer Technology*, "Commercial Processes for the Manufacture of Superabsorbent Polymers," pp. 252-258, pp. 71-103. New York: John Wiley & Sons, Inc., 1998.
U.S. Appl. No. 12/868,453, filed Aug. 25, 2010, now U.S. Pat. No. 8,481,159.
U.S. Appl. No. 13/063,075, filed Mar. 9, 2011.
U.S. Appl. No. 13/053,929, filed Mar. 22, 2011.
U.S. Appl. No. 13/070,173, filed Mar. 23, 2011.
U.S. Appl. No. 13/391,711, filed Apr. 22, 2012.
International Search Report in international application No. PCT/EP2011/061032, dated Oct. 25, 2011.

\* cited by examiner

*Primary Examiner* — Peter S Vasat
(74) *Attorney, Agent, or Firm* — Marshall, Gerstein & Borun LLP

(57) ABSTRACT

The present invention relates to ultrathin fluid-absorbent cores comprising a substrate layer, water-absorbent polymer particles and an adhesive, wherein the water-absorbent polymer particles comprise a basic salt of a polyvalent metal cation and a monovalent carboxylic acid anion on the surface and the wet SAP shake out of water-absorbent polymer particles out of the fluid-absorbent core is less than 10% by weight.

15 Claims, No Drawings

ULTRATHIN FLUID-ABSORBENT CORES

CROSS-REFERENCE TO RELATED APPLICATIONS

This application claims the benefit of U.S. Provisional Patent Application No. 61/360,932, filed Jul. 2, 2010, incorporated herein by reference in its entirety.

The present invention relates to ultrathin fluid-absorbent cores comprising a substrate layer, water-absorbent polymer particles and an adhesive, wherein the wet SAP shake out (SAPLoss) of water-absorbent polymer particles out of the fluid-absorbent core is less than 10% by weight.

The production of fluid-absorbent articles is described in the monograph "Modern Superabsorbent Polymer Technology", F. L. Buchholz and A. T. Graham, Wiley-VCH, 1998, pages 252 to 258.

Fluid-absorbent articles such as disposable diapers typically comprise an upper liquid-pervious layer, a lower liquid-impervious layer, and a fluid-absorbent core between the upper and the lower layer. The fluid-absorbent cores typically comprise water-absorbent polymers and fibers.

Ultrathin fluid absorbent cores can be formed by immobilization of water-absorbent polymer particles on a nonwoven using hotmelt adhesives, i.e. forming longitudinal strips or discrete spots. Other patterns of the water-absorbent polymer particles are also possible.

The preparation of ultrathin fluid-absorbent cores is described, for example, in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/0135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2.

The production of water-absorbent polymer particles is likewise described in the monograph "Modern Superabsorbent Polymer Technology", F. L. Buchholz and A. T. Graham, Wiley-VCH, 1998, pages 71 to 103. Water-absorbent polymer particles are also referred to as "superabsorbent polymers" or "superabsorbents".

The prior PCT application having the reference number PCT/EP2010/053657 describes the use of basic salts of a trivalent metal cation and a monovalent carboxylic acid anion as coating agent for the preparation of postcrosslinked water-absorbent polymer particles.

It was an object of the present invention to provide ultrathin fluid-absorbent cores having improved properties, i.e. a reduced wet SAP shake out (SAPLoss) of water-absorbent polymer particles.

The object is achieved by fluid-absorbent cores comprising a substrate layer, at least 75% by weight of water-absorbent polymer particles, and an adhesive, wherein the water-absorbent polymer particles comprise a basic salt of a polyvalent metal cation and a monovalent carboxylic acid anion on the surface and the wet SAP shake out (SAPLoss) of water-absorbent polymer particles out of the fluid-absorbent core is less than 10% by weight.

The fluid-absorbent core comprises preferably at least 80% by weight, more preferably at least 83% by weight, most preferably at least 85% by weight, of water-absorbent polymer particles.

The fluid-absorbent core comprises preferably not more than 15% by weight, more preferably not more than 10% by weight, most preferably not more than 7% by weight, of the adhesive.

In a preferred embodiment of the present invention a pressure sensitive adhesive is used that means that no solvent, water, or heat is needed to activate the adhesive. The substrate layer is preferably a nonwoven layer or a tissue paper. Further, the fluid-absorbent cores can comprise two or more layers of water-absorbent polymer particles. The water-absorbent polymer particles are preferably placed in discrete regions of the fluid-absorbent core.

The wet SAP shake out (SAPLoss) of water-absorbent polymer particles out of the fluid-absorbent core is preferably less than 8% by weight, more preferably less than 6% by weight, most preferably less than 5% by weight.

The present invention is based on the finding that the wet SAP shake out (SAPLoss) of water-absorbent polymer particles can be reduced by using water-absorbent polymer particles having a coating with at least one specified basic salt and an adhesive.

In the basic salts, not all hydroxide groups eliminable as hydroxyl anions (OH−) in aqueous solutions in the salt-forming bases are replaced by acid groups.

The molar ratio of polyvalent metal cation to monovalent carboxylic acid anion in the basic salts is typically from 0.4 to 10, preferably from 0.5 to 5, more preferably from 0.6 to 2.5, most preferably from 0.8 to 1.2.

The amount of polyvalent metal cation used is preferably from 0.001 to 0.05 mol, more preferably from 0.002 to 0.02 mol, most preferably from 0.003 to 0.01 mol, each based on 100 g of the water-absorbing polymer particles to be coated.

In a preferred embodiment of the present invention basic salts of a trivalent metal cation and a monovalent carboxylic acid anion are used.

The trivalent metal cation is preferably a metal cation of the third main group, of the third transition group or of the lanthanide group of the periodic table of the elements, more preferably aluminium, scandium, yttrium, lanthanum or cerium, most preferably aluminium.

In a preferred embodiment of the present invention basic salts of a polyvalent metal cation and an unsubstituted or substituted acetic acid anion are used.

Substituted acetic acid means any substituent with the exemption of directly bonded carbon. So, acids like propionic acid or lactic acid do not fall under the definition of a substituted acetic acid.

The unsubstituted or substituted acetic acid anion is preferably an acetic acid anion and/or an aminoacetic acid anion.

In a more preferred embodiment of the present invention basic salts of a trivalent metal cation and an unsubstituted or substituted acetic acid anion are used.

Suitable basic salts are, for example, basic aluminium acetate and/or basic aluminium aminoacetate. Very particular preference is given to aluminium monoacetate (CAS No. [7360-44-3]) and/or aluminium monoaminoacetate (CAS No. [13682-92-3]).

The method of applying the basic salts of a polyvalent metal cation and a monovalent carboxylic acid anion is not subject to any restriction. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US), Schugi Flexomix® (Hosokawa Micron BV; Doetinchem; the Netherlands), Hosokawa Bepex® Horizontal Paddle Dryers (Hosokawa Micron GmbH; Leingarten; Germany), Hosokawa Bepex®

Disc Dryers (Hosokawa Micron GmbH; Leingarten; Germany) and Nara Paddle Dryers (NARA Machinery Europe; Frechen; Germany).

The basic salt is preferably used as an aqueous solution or slurry. The aqueous solutions are prepared, for example, by dissolving the appropriate basic salts in an aqueous solvent, for example water. However, it is also possible to mix appropriate amounts of the corresponding base, for example aluminium hydroxide, and the corresponding acid, for example acetic acid, in an aqueous solvent, for example water.

The water content of the aqueous solution is preferably from 60 to 98% by weight, more preferably from 65 to 90% by weight, most preferably from 70 to 85% by weight. In order to increase the solubility in the aqueous solution, the solution can be prepared and used at elevated temperature.

The aqueous solutions for use in accordance with the invention, comprising at least one basic salt, may tend to precipitate in the course of prolonged storage. The solutions therefore advantageously comprise at least one stabilizer. Suitable stabilizers are, for example, polyhydric alcohols such as mannitol and glycerol, soluble carbohydrates such as disaccharides and monosaccharides, polyvalent inorganic acids such as boric acid and phosphoric acid, hydroxycarboxylic acids or salts thereof, such as citric acid, lactic acid and tartaric acid or salts thereof, dicarboxylic acids or salts thereof, such as adipic acid and succinic acid, and urea and thiourea. Preference is given to using boric acid and/or aspartic acid as the stabilizer.

In a preferred embodiment of the present invention, the aqueous solution comprising the basic salt and an aqueous solution comprising a surface postcrosslinker are applied to the water-absorbing polymer particles in the same mixer. The aqueous solutions can be metered in separately or else as a combined solution.

In a further preferred embodiment of the present invention, the basic salt is applied only after the surface post-crosslinking. For the coating, it is possible to use either aqueous solutions or the corresponding undissolved salts, for example dry aluminium monoacetate.

The present invention further provides fluid-absorbent articles which comprise the inventive fluid-absorbent cores.

DETAILED DESCRIPTION OF THE INVENTION

A. Definitions

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" refers to a fluid-absorbent composition comprising a fibrous material and water-absorbent polymer particles. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein, the term "x-dimension" refers to the length, and the term "y-dimension" refers to the width of the fluid-absorbent composition, layer, core or article. Generally, the term "x-y dimension" refers to the plane, orthogonal to the height or thickness of the fluid-absorbent composition, layer, core or article.

As used herein, the term "z-dimension" refers to the dimension orthogonal to the length and width of the fluid-absorbent composition, layer, core or article. Generally, the term "z-dimension" refers to the height of the fluid-absorbent composition.

As used herein, the term "chassis" refers to fluid-absorbent material comprising the upper liquid-pervious layer and the lower liquid-impervious layer.

As used herein, the term "basis weight" indicates the weight of the fluid-absorbent core per square meter and it includes the chassis of the fluid-absorbent article. The basis weight is determined at discrete regions of the fluid-absorbent core: the front overall average is the basis weight of the fluid-absorbent core 5.5 cm forward of the center of the core to the front distal edge of the core; the insult zone is the basis weight of the fluid-absorbent core 5.5 cm forward and 0.5 cm backwards of the center of the core; the back overall average is the basis weight of the fluid-absorbent core 0.5 cm backward of the center of the core to the rear distal edge of the core.

As used herein, the term "density" indicates the weight of the fluid-absorbent core per volume and it includes the chassis of the fluid-absorbent article. The density is determined at discrete regions of the fluid-absorbent core: the front overall average is the density of the fluid-absorbent core 5.5 cm forward of the center of the core to the front distal edge of the core; the insult zone is the density of the fluid-absorbent core 5.5 cm forward and 0.5 cm backwards of the center of the core; the back overall average is the density of the fluid-absorbent core 0.5 cm backward of the center of the core to the rear distal edge of the core.

Further, it should be understood, that the term "upper" refers to fluid-absorbent compositions which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the composition which is furthermost away from the wearer of the fluid-absorbent article, hereinafter described as "lower liquid-impervious layer".

As used herein, the term "liquid-pervious" refers to a substrate, layer or laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

Fluid-absorbent articles comprising more than one fluid-absorbent core, in a preferred manner comprising a double-core system including an upper core and a lower core, hereinafter called "primary core" and "secondary core".

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "section" or "zone" refers to a definite region of the fluid-absorbent composition.

As used herein, the term "article" refers to any three-dimensional solid material being able to acquire and store fluids discharged from the body. Preferred articles according to the present invention are disposable fluid-absorbent articles that are designed to be worn in contact with the body of a user such as disposable fluid-absorbent pantiliners, sanitary napkins, catamenials, incontinence inserts/pads, diapers, training pant diapers, breast pads, interlabial inserts/pads and the like.

As used herein, the term in "body fluids" refers to any fluid produced and discharged by human or animal body, such as urine, menstrual fluids, faeces, vaginal secretions and the like.

B. Water-Absorbent Polymer Particles

The water-absorbent polymer particles are preferably prepared by polymerizing a monomer solution or suspension comprising a) at least one ethylenically unsaturated monomer which bears acid groups and may be at least partly neutralized, b) at least one crosslinker, c) at least one initiator, d) optionally one or more ethylenically unsaturated monomers copolymerizable with the monomers mentioned under a), e) optionally one or more water-soluble polymers, and f) water, and are typically water-insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

The content of acrylic acid and/or salts thereof in the total amount of monomers a) is preferably at least 50 mol %, more preferably at least 90 mol %, most preferably at least 95 mol %.

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Examples for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tatrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The polymer gel is then preferably dried with a belt dryer until the residual moisture content is preferably from 0.5 to 15% by weight, more preferably from 1 to 10% by weight, most preferably from 2 to 8% by weight, the residual moisture content being determined by the EDANA recommended test method No. WSP 230.2-05 "Moisture Content". In the case of too high a residual moisture content, the dried polymer gel has too low a glass transition temperature Tg and can be processed further only with difficulty. In the case of too low a residual moisture content, the dried polymer gel is too brittle and, in the subsequent comminution steps, undesirably large amounts of polymer particles with an excessively low particle size are obtained (fines). The solids content of the gel before the drying is preferably from 25 to 90% by weight, more preferably from 35 to 70% by weight, most preferably from 40 to 60% by weight. Optionally, it is, however, also possible to use a fluidized bed dryer or a paddle dryer for the drying operation.

Thereafter, the dried polymer gel is ground and classified, and the apparatus used for grinding may typically be single or multistage roll mills, preferably two or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of the EDANA recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When a kneading reactor is used for the polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until within an apparatus connected downstream of the polymerization reactor, for example an extruder, the excessively small polymer particles can be incorporated into the resulting polymer gel only with difficulty. Excessively small polymer particles which have been insufficiently incorporated, however, become detached again from the dried polymer gel during the grinding, and are therefore removed again in the classification and increase the amount of excessively small polymer particles to be recycled.

The proportion of particles having a particle size of at most 850 µm is preferably at least 90% by weight, more preferably at least 95% by weight, most preferably at least 98% by weight.

Advantageously, the proportion of polymer particles with a particle size of at most 600 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1,2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are glycerol, ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably from 0.001 to 2% by weight, more preferably from 0.02 to 1% by weight, most preferably from 0.05 to 0.2% by weight, based in each case on the polymer particles.

In the present invention, before, during or after the surface postcrosslinking, in addition to the surface postcrosslinkers, at least one basic salt of a trivalent metal cation and a monovalent carboxylic acid anion is applied to the particle surface.

It will be appreciated that it is also additionally possible to use further polyvalent cations. Suitable polyvalent cations are, for example, divalent cations such as the cations of zinc, magnesium, calcium, iron and strontium, trivalent cations such as the cations of aluminium, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminium sulfate and aluminium lactate are preferred. It is also possible to use polyamines as further polyvalent cations.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behaviour and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact dryers, more preferably paddle dryers, most preferably disk dryers. Suitable dryers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany) and Nara Paddle Dryers (NARA Machinery Europe; Frechen; Germany). Moreover, it is also possible to use fluidized bed dryers.

The drying can be effected in the mixer itself, by heating the jacket or blowing in warm air. Equally suitable is a downstream dryer, for example a shelf dryer, a rotary tube oven or a heatable screw. It is particularly advantageous to mix and dry in a fluidized bed dryer.

Preferred drying temperatures are in the range from 100 to 250° C., preferably from 120 to 220° C., more preferably from 130 to 210° C., most preferably from 150 to 200° C. The preferred residence time at this temperature in the reaction mixer or dryer is preferably at least 10 minutes, more preferably at least 20 minutes, most preferably at least 30 minutes, and typically at most 60 minutes.

To further improve the properties, the surface postcrosslinked polymer particles can be coated or subsequently moistened.

The subsequent moistening is carried out preferably at from 30 to 80° C., more preferably at from 35 to 70° C. and most preferably at from 40 to 60° C. At excessively low temperatures, the water-absorbing polymer particles tend to form lumps, and, at higher temperatures, water already evaporates noticeably. The amount of water used for subsequent moistening is preferably from 1 to 10% by weight, more preferably from 2 to 8% by weight and most preferably from 3 to 5% by weight. The subsequent moistening increases the mechanical stability of the polymer particles and reduces their tendency to static charging.

Suitable coatings for improving the swell rate and the saline flow conductivity (SFC) and/or gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

Subsequently, the surface postcrosslinked polymer particles can be classified again to remove excessively small and/or excessively large polymer particles which are recycled into the process.

The water-absorbent polymer particles useable for the fluid-absorbent cores according to the invention have a centrifuge retention capacity (CRC) of typically at least 20 g/g, preferably at least 25 g/g, preferentially at least 28 g/g, more preferably at least 30 g/g, most preferably at least 32 g/g. The centrifuge retention capacity (CRC) of the water-absorbent polymer particles is typically less than 60 g/g.

The water-absorbent polymer particles useable for the fluid-absorbent cores according to the invention have a saline flow conductivity (SFC) of typically at least $30 \times 10^{-7}$ cm$^3$s/g, preferably at least $50 \times 10^{-7}$ cm$^3$s/g, preferentially at least $70 \times 10^{-7}$ cm$^3$s/g, more preferably at least $90 \times 10^{-7}$ cm$^3$s/g, most preferably at least $100 \times 10^{-7}$ cm$^3$s/g, and typically not more than $300 \times 10^{-7}$ cm$^3$ s/g.

The water-absorbent polymer particles useable for the fluid-absorbent cores according to the invention have a free swell gel bed permeability (GBP) of typically at least 20 Darcies, preferably at least 50 Darcies, preferentially at least 70 Darcies, more preferably at least 90 Darcies, most preferably at least 100 Darcies, and typically not more than 250 Darcies.

Preferred water-absorbent polymer particles are polymer particles having a centrifuge retention capacity (CRC) of at least 20 g/g, preferably of at least 25 g/g, more preferably of at least 28 g/g, most preferably of at least 30 g/g, and a saline flow conductivity (SFC) of at least $20 \times 10^{-7}$ cm$^3$s/g, preferably of at least $50 \times 10^{-7}$ cm$^3$s/g, more preferably of at least $70 \times 10^{-7}$ cm$^3$s/g, most preferably of at least $90 \times 10^{-7}$ cm$^3$s/g.

Also preferred water-absorbent polymer particles are polymer particles having a centrifuge retention capacity (CRC) of at least 20 g/g, preferably of at least 25 g/g, more preferably of at least 28 g/g, most preferably of at least 30 g/g, and free swell gel bed permeability (GBP) of at least 20 Darcies, preferably of at least 50 Darcies, more preferably of at least 70 Darcies, most preferably of at least 90 Darcies.

C. Fluid-Absorbent Articles

The fluid-absorbent article comprises of
(A) an upper liquid-pervious layer
(B) a lower liquid-impervious layer
(C) a fluid-absorbent core between (A) and (B) comprising an optional core cover, a fluid-storage layer comprising
   at least 75% by weight water-absorbent polymer particles and an adhesive;
   preferably at least 80% by weight water-absorbent polymer particles and an adhesive;
   more preferably at least 83% by weight water-absorbent polymer particles and an adhesive;
   most preferably at least 85% by weight water-absorbent polymer particles and an adhesive;
   and an optional dusting layer
(D) an optional acquisition-distribution layer between (A) and (C), comprising
   at least 80% by weight fibrous material and water-absorbent polymer particles;
   preferably at least 85% by weight fibrous material and water-absorbent polymer particles;
   more preferably at least 90% by weight fibrous material and water-absorbent polymer particles;
   most preferably at least 95% by weight fibrous material and water-absorbent polymer particles;

(E) an optional tissue layer disposed immediately above and/or below (C); and (F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious layer may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural fibers or synthetic fibers or any combination thereof. Preferred materials are polyester, rayon and blends thereof, polyethylene, and polypropylene.

The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e.g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of rising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermal treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behavior of the layer. If there is further some profiled structure integrated, the acquisition-distribution behavior can be directed depending on the three-dimensional structure of the layer. Thus 3D-polyethylene in the function of liquid-pervious layer is preferred.

Thus, suitable liquid-pervious layers (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious layers (A) extend partially or wholly across the fluid-absorbent structure and can extend into and/or form part of all the preferred sideflaps, side wrapping elements, wings and ears.

Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pyjamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious layer (B) is made of nonwoven comprising hydrophobic materials, e.g. synthetic fibers or a liquid-impervious polymeric film comprising plastics e.g. polyethylene. The thickness of the liquid-impervious layer is preferably 15 to 30 µm.

Further, the liquid-impervious layer (B) is preferably made of a laminate of nonwoven and plastics comprising a nonwoven having a density of 12 to 15 gsm and a polyethylene layer having a thickness of about 10 to 20 µm.

The typically liquid-impervious layer (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

The top view area of the fluid-absorbent core (C) is preferably at least 200 cm$^2$, more preferably at least 250 cm$^2$, most preferably at least 300 cm$^2$. The top view area is the part of the core that is face-to-face to the upper liquid-pervious layer.

The fluid-absorbent core comprises a substrate layer, i.e. a nonwoven layer or a tissue paper, water-absorbent polymer particles, and an adhesive.

Suitable nonwoven layers for the present invention include those made using synthetic polymeric fibers. The synthetic polymeric fibers may be formed from any polymeric material capable of forming fibers which fibers can be formed into a nonwoven layer. Suitable polymeric material from which the synthetic polymeric fibers may be formed include polyolefins, such as polyethylene, polypropylene, and the like, polyesters such as polyethylene terephthalate and the like, polyamides such as nylon 6, nylon 6,6, poly (iminocarboxylpentamethylene) and the like, acrylics, and modified cellulosic material, such as cellulose acetate and rayon; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the nonwoven layer is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example, of from about 25 to 75 mm or short cut into lengths of from about 1 to 25 mm. The synthetic polymeric fibers may suitably have a maximum cross-sectional dimension of from about 0.5 to 50 µm as determined by microscopic measurement using an optical microscope and a calibrated stage micrometer or by measurement from Scanning Electron photomicrographs.

The nonwoven layers may be formed directly through a spunbond or meltblown process, or by carding or air-laying staple or short cut fibers. Other methods of forming nonwoven layers known to those skilled in the art may be suited for use in the present invention. The nonwoven layer may subsequently be bonded to enhance structural integrity. Methods of bonding nonwoven layers are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known to those skilled in the art as bicomponent fibers.

The nonwoven layer may be formed from a single type of synthetic polymeric fiber or may contain synthetic polymeric fibers formed from different polymeric materials, having different fiber lengths or maximum cross-sectional dimensions. For example, the nonwoven layer may comprise a mixture of (1) bicomponent fibers having a polyethylene sheath and a polypropylene core which bicomponent fibers have a maximum cross-sectional dimension of about 20 µm and a length of about 38 mm and (2) polyester fibers, i.e. polyethylene terephthalate, having a maximum cross-sectional dimension of about 25 µm and a length of about 38 mm. Fibers 1 and 2 may be combined in a weight ratio of from 1:99 to 99:1. The fibers may be uniformly mixed or may be concentrated at opposite planar surfaces of the nonwoven layer.

The nonwoven layer suitably comprises preferably from about 20 to 100% by weight, more preferably from about 25 to 100% by weight, most preferably from about 50 to 100% by weight, synthetic polymeric fibers. In addition to the synthetic polymeric fibers, the nonwoven layer may contain from about 90 to 0% by weight of a non-synthetic polymeric fiber such as wood pulp fluff cotton linters, cotton, and the like.

In one preferred embodiment, the nonwoven layer contains synthetic polymeric fibers which are formed from a polymeric material having a high wet modulus. The importance of the modulus of a material is discussed in the monograph "Absorbency", P. K. Chatterjee, Elsevier, 1985. A polymeric material will be considered to have a high wet modulus when it has a wet modulus greater than about 80% of its dry modulus as determined by the ASTM test method D 2101-91 using modified gauge lengths. It is often desired to form the synthetic polymeric fibers of the nonwoven layer from a polymeric material having a high wet modulus because such materials generally form nonwoven layers which possess a relatively high degree of wet resiliency. The wet resilience of a nonwoven layer is related to the pore structure (while under a load) of the nonwoven layer. As will be discussed in greater detail below, it is often desired that the nonwoven layer have a relatively high degree of wet resilience.

The pore structure (while under a load) of a fibrous structure formed from fibers of a polymeric material will, as discussed above, relate to the wet and/or dry modulus of the constituent fibers. Wet modulus of the constituent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the monograph "Physical Properties of Textile Fibers", W. E. Morton and J. W. S. Hearl, The Textile Institute, 1975, can be used.

As a general rule, the polymeric materials from which the synthetic polymeric fibers of the nonwoven layer are formed will be inherently hydrophobic. As used herein, a polymeric material will be considered to be "inherently" hydrophobic or hydrophilic when the polymeric material, free from any surface modifications or treatments, e.g., surface active agents, spin finishes, blooming agents, etc., is hydrophobic or hydrophilic, respectively.

When the synthetic polymeric fibers of the nonwoven layer are formed from a polymeric material which is inherently hydrophobic, it is often desirable to treat the fibers with a surface modifying material to render the surface of the fiber hydrophilic. For example, a surfactant may be applied to the fibers.

The nonwoven layer may also comprise hydrophilic fibers. The hydrophilic materials may be inherently hydrophilic such as cellulosic fibers such as wood pulp fluff, cotton linters, and the like, regenerated cellulose fibers such as rayon, or certain nylon copolymers such as poly (pentamethylenecarbonamide) (nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydrophilizing fibers formed from hydrophobic materials are known and suited for use in the present invention.

Methods of providing inherently hydrophilic fibers such as wood pulp fluff are known. Hydrophobic fibers which can be treated to possess a hydrophilic surface are suitably formed by processes known to those skilled in the art. If the hydrophilic fibers are hydrophobic fibers which have been treated to possess a hydrophilic surface, the fibers will suitably have a fiber length and maximum cross-sectional dimension as set forth above. If the hydrophilic fibers are inherently hydrophilic such as wood pulp fluff, rayon, cotton, cotton linters and the like, the fibers will generally have a length of from about 1.0 to 50 mm and a maximum cross-sectional dimension of from about 0.5 to 100 μm.

The nonwoven layer suitably comprises preferably from about 10 to 100% by weight, more preferably from about 30 to 100% by weight, most preferably from about 55 to 100% by weight of hydrophilic fibers, preferably inherently hydrophilic fibers. In addition to the hydrophilic fibers, the nonwoven layer may contain from about 90 to 0% by weight of a high wet modulus, preferably inherently hydrophobic, fibers. The nonwoven layer may be formed from a single type of hydrophilic fiber or may contain hydrophilic fibers having different compositions, lengths and maximum cross-sectional dimensions.

In one preferred embodiment, the nonwoven layer is formed from air laid cellulosic fibers such as wood pulp fluff. Wood pulp fluff fibers are preferred for use due to their ready availability and due to the fact that the fibers are relatively inexpensive compared to synthetic polymeric fibers.

The nonwoven layer suitably has a basis weight of preferably from about 10 to 200 gsm, more preferably from about 20 to 150 gsm, most preferably from about 25 to 125 gsm.

The nonwoven layer suitably has a density of preferably from about 0.04 to 0.20 $g/cm^3$, more preferably from about 0.06 to 0.16 $g/cm^3$, most preferably from about 0.08 to 0.14 $g/cm^3$.

Typically the fluid-absorbent cores may contain a single type of water-absorbent polymer particles or may contain water-absorbent polymer particles derived from different kinds of water-absorbent polymer material. Thus, it is possible to add water-absorbent polymer particles from a single kind of polymer material or a mixture of water-absorbent polymer particles from different kinds of polymer materials, e.g. a mixture of regular water-absorbent polymer particles, derived from gel polymerization with water-absorbent polymer particles, derived from dropletization polymerization. Alternatively it is possible to add water-absorbent polymer particles derived from inverse suspension polymerization.

Alternatively it is possible to mix water-absorbent polymer particles showing different feature profiles. Thus, the fluid-absorbent core may contain water-absorbent polymer particles with uniform pH value, or it may contain water-absorbent polymer particles with different pH values, e.g. two- or more component mixtures from water-absorbent polymer particles with a pH in the range from about 4.0 to about 7.0. Preferably, applied mixtures deriving from mixtures of water-absorbent polymer particles got from gel polymerization or inverse suspension polymerization with a pH in the range from about 4.0 to about 7.0 and water-absorbent polymer particles got from dropletization polymerization.

The fluid-absorbent core comprises at least 75% by weight, preferably at least 80% by weight, more preferably at least 83% by weight, most preferably at least 85% by weight, of water-absorbent polymer particles.

The quantity of water-absorbent polymer particles within the fluid-absorbent core is preferably from 3 to 20 g, more preferably from 6 to 14 g, most preferably from 8 to 12 g in the case of maxi-diapers, and in the case of incontinence products up to about 50 g.

The types of adhesives are not particularly limited. A wide variety of thermoplastic compositions are suitable for use as pressure sensitive adhesives in the present invention.

Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefine or styrene block copolymer and mixture of waxes.

Suitable thermoplastic polymers are styrenic block copolymers including A-B-A triblock segments, A-B diblock segments and (A-B), radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

The construction of the fluid-absorbent cores is made and controlled by the discrete application of adhesives as known to people skilled in the art. Examples would be e.g. Dispomelt 505B, Dispomelt Cool 1101, as well as other specific function adhesives manufactured by National Starch or Henkel.

Ultrathin fluid-absorbent cores are be formed by immobilization of water-absorbent polymer particles on a substrate layer using adhesives. Preferably the water-absorbent polymer particles form longitudinal strips or discrete spots. Other patterns of the water-absorbent polymer particles are also possible.

Typically, the water-absorbent polymer particles form a discontinuous layer on the substrate layer, i.e. a nonwoven layer, covered by a thermoplastic composition as adhesive forming discrete cavities, so that the water-absorbent polymer particles are immobilized.

It is also possible to use a second substrate layer that comprises an adhesive instead of the thermoplastic composition.

In a preferred embodiment the ultrathin fluid-absorbent cores comprise at least two layers of immobilized water-absorbent polymer particles.

Suitable fluid-absorbent cores may also include layers, which are formed by the process of manufacturing the fluid-absorbent article. The layered structure may be formed by subsequently generating the different layers in z-direction.

Alternatively a core-structure can be formed from two or more preformed layers to get a layered fluid-absorbent core. These uniform or different layers can be fixed to each other at their adjacent plane surfaces. Alternatively, the layers may be combined in a way that a plurality of chambers is formed, in which separately water-absorbent polymer material is incorporated.

Further a composite structure can be formed from a carrier layer (e.g. a polymer film), onto which the water-absorbent polymer material is affixed. The fixation can be done at one side or at both sides. The carrier layer may be pervious or impervious for body-fluids.

Typically fluid-absorbent articles comprising at least an upper liquid-pervious layer (A), at least a lower liquid-impervious layer (B) and at least one fluid-absorbent core between the layer (A) and the layer (B) besides other optional layers. The addition of a second fluid-absorbent core to the first fluid-absorbent core offers more possibilities in body fluid transfer and distribution. Moreover higher quantities of discharged body fluids can be retained. Having the opportunity of combining several layers showing different water-absorbent polymer concentration and content, it is possible to reduce the thickness of the fluid-absorbent article to a minimum even if there are several fluid-absorbent cores included.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

These layers or foldings are preferably joined to each e.g. by addition of adhesives or by mechanical, thermal or ultrasonic bonding or combinations thereof. Water-absorbent polymer particles may be comprised within or between the individual layers, e.g. by forming separate water-absorbent polymer-layers.

The fluid-absorbent core may comprise additional additives typically present in fluid-absorbent articles known in the art. Exemplary additives are odor control additives and wetness indication additives.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclohexaneacetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevo-carveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, and Zn, enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from about 0.5 to about 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of about 1 to 5% by weight related to the weight of the fluid-absorbent core.

The basis weight of the fluid-absorbent core is preferably in the range of 400 to 1200 gsm. The density of the fluid-absorbent core is preferably in the range of 0.1 to 0.50 g/cm$^3$. The thickness of the fluid-absorbent core is in the case of diapers preferably in the range of 1 to 5 mm, in the case of incontinence products preferably in the range of 3 to 15 mm.

Optional Acquisition-Distribution Layer (D)

An optional acquisition-distribution layer (D) is located between the upper layer (A) and the fluid-absorbent core (C) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer comprises fibrous material and optionally water-absorbent polymer particles.

The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof. Thus, suitable acquisition-distribution layers may contain cellulosic fibers, in particular wood pulp fluff. Examples of further suitable hydrophilic, hydrophobic fibers, as well as modified or unmodified natural fibers are given in the chapter "Liquid-pervious Layer (A)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of coatings and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by crosslink bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious Layer (A)" above. 3D-polyethylene in the function of acquisition-distribution layer is preferred.

Further, as in the case of cellulosic fibers, hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Preferred acquisition-distribution layers comprise fibrous material and water-absorbent polymer particles distributed within. The water-absorbent polymer particles may be added during the process of forming the layer from loose fibers, or, alternatively, it is possible to add monomer solution after the formation of the layer and polymerize the coating solution by means of UV-induced polymerization technologies. Thus, "in situ"-polymerization is a further method for the application of water-absorbent polymers.

Thus, suitable acquisition-distribution layers comprising from 80 to 100% by weight fibrous material and from 0 to 20% by weight water-absorbent polymer particles; preferably from 85 to 99.9% by weight fibrous material and from 0.1 to 15% by weight water-absorbent polymer particles; more preferably from 90 to 99.5% by weight fibrous material and from 0.5 to 10% by weight water-absorbent polymer particles; and most preferably from 95 to 99% by weight fibrous material and from 1 to 5% by weight water-absorbent polymer particles.

Preferred acquisition-distribution layers show basis weights in the range from 20 to 200 gsm, most preferred in the range from 40 to 50 gsm, depending on the concentration of water-absorbent polymer particles.

Optional Tissue Layer (E)

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearer's body, e.g. the waist and the legs to improve containment and fit. Leg elastics are placed between the outer and inner layers or the fluid-absorbent article, or between the outer cover and the bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system includes tape tabs, landing zone, elastomerics, pull ups and the belt system.

At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attacked to the backing material.

Thus suitable landing zones can be made by spunbonding. Spunbonded nonwovens are made from melt-spun fibers formed by extruding molten thermoplastic material. Preferred is bioriented polypropylene (BOPP), or brushed/closed loop in the case of mechanical closing systems.

Further, suitable mechanical closing systems including elastic units serving as a flexible waist band for fluid-absorbents articles, such as pants or pull-ups. The elastic units enabling the fluid-absorbent article to be pulled down by the wearer as e.g. a training pant.

Suitable pants-shaped fluid-absorbent article has front section, rear section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat.

Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single- or double fluid-absorbent core-system.

Suitable fluid-storage layers of the fluid-absorbent core comprising homogenous or inhomogeneous mixtures of fibrous materials comprising water-absorbent polymer particles homogeneously or inhomogeneously dispersed in it. Suitable fluid-storage layers of the fluid-absorbent core including a layered fluid-absorbent core-system comprising homogenous mixtures of fibrous materials and optionally comprising water-absorbent polymer particles, whereby each of the layers may be prepared from any fibrous material by means known in the art.

In order to immobilize the water-absorbent polymer particles, the adjacent layers are fixed by the means of thermoplastic materials, thereby building connections throughout the whole surface or alternatively in discrete areas of junction. For the latter case, cavities or pockets are built carrying the fluid-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

The water-absorbent polymer particles and the fluid-absorbent articles are tested by means of the test methods described below.
Methods:

The measurements should, unless stated otherwise, be carried out at an ambient temperature of 23±2° C. and a relative atmospheric humidity of 50±10%. The water-absorbent polymers are mixed thoroughly before the measurement.
Saline Flow Conductivity (SFC)

The saline flow conductivity is, as described in EP 0 640 330 A1, determined as the gel layer permeability of a swollen gel layer of water-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$\text{SFC } [cm^3 s/g] = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to $t=0$, $L0$ is the thickness of the gel layer in cm, d is the density of the NaCl solution in $g/cm^3$, A is the surface area of the gel layer in $cm^2$ and WP is the hydrostatic pressure over the gel layer in $dyn/cm^2$.
Free Swell Gel Bed Permeability (GBP)

The method to determine the free swell gel bed permeability is described in US 2005/0256757, paragraphs [0061] to [0075].
Centrifuge Retention Capacity (CRC)

The centrifuge retention capacity of the water-absorbent polymer particles is determined by the EDANA recommended test method No. WSP 241.2-05 "Centrifuge Retention Capacity", wherein for higher values of the centrifuge retention capacity lager tea bags have to be used.
Wet SAP Shake Out (SAPLoss)

The wet SAP shake out of water-absorbent polymer particles is determined using a rectangle core sample having a size of 7 inch×4 inch (17.8 cm×10.2 cm) that is cut from the center of a fluid-absorbent core. The weight of the cut core sample is recorded as Dry Weight ($W_{dry}$). The dry core sample is laid in a pan and 10 g of 0.9% NaCl solution per gram of Dry Weight are added to the core sample homogeneously. Five minutes after all free liquid has been absorbed by the core sample, the wet core sample is weighted and recorded as Before Shake Wet Weight ($W_{b\text{-}wet}$). The wet core sample is carefully placed on top of an 850 micron U.S.A. standard testing sieve (VWR International LLC; Arlington Heights; U.S.A.). The sieve with the wet core sample is installed on a Retsch® AS 200 sieve shaker (Retsch GmbH; Haan; Gemany) and shaken at pre-set amplitude of 2.00 for 5 minutes. Next, the wet core sample is picked up on the short end and vertically transferred to a weighting pan. The wet core sample is recorded as After Shake Wet Weight ($W_{a\text{-}wet}$). The wet SAP shake out (SAPLoss) is calculated as follows:

$$SAPLoss[wt. \%] = \frac{W_{b-wet} - W_{a-wet}}{W_{b-wet}}$$

The EDANA test methods are obtainable, for example, from the EDANA, Avenue Eugène Plasky 157, B-1030 Brussels, Belgium.

EXAMPLES

Preparation of the Base Polymer

Example 1

By continuously mixing water, 50% by weight sodium hydroxide solution and acrylic acid, a 40.0% by weight acrylic acid/sodium acrylate solution was prepared, such that the degree of neutralization was 71.0 mol %. After the mixing of the components, the monomer solution was cooled continuously by a heat exchanger.

The ethylenically polyunsaturated crosslinker used is polyethylene glycol-400 diacrylate (diacrylate of a polyethylene glycol having a mean molar mass of 400 g/mol). The amount used was 1.6 kg per t of monomer solution.

To initiate the free-radical polymerization, the following components were used: hydrogen peroxide (1.00 kg (0.25% strength by weight) per t of monomer solution), sodium peroxodisulfate (1.50 kg (30% strength by weight) per t of monomer solution) and ascorbic acid (1.05 kg (1% strength by weight) per t of monomer solution).

The throughput of the monomer solution was 20 t/h.

The individual components were metered continuously into a List Contikneter continuous kneader with capacity 6.3 m³ (from List, Arisdorf, Switzerland) in the following amounts:

| | |
|---|---|
| 20 t/h | of monomer solution |
| 32 kg/h | of polyethylene glycol-400 diacrylate |
| 50 kg/h | of hydrogen peroxide solution/sodium peroxodisulfate solution |
| 21 kg/h | of ascorbic acid solution |

Between the addition points for crosslinker and initiators, the monomer solution was inertized with nitrogen.

At the end of the reactor, 1300 kg/h of removed undersize having a particle size of less than 150 μm were additionally metered in.

At the feed, the reaction solution had a temperature of 35° C. The reactor was operated with a rotational speed of the shafts of 38 rpm. The residence time of the reaction mixture in the reactor was 15 minutes.

After polymerization and gel comminution, the aqueous polymer gel was introduced into a belt dryer. The residence time on the dryer belt was approx. 37 minutes.

The dried hydrogel was ground and screened off to 150 to 850 μm. The base polymer thus prepared had a centrifuge retention capacity (CRC) of 39.5 g/g.

Example 2

A double-wall 10 l glass reactor with mechanical stirring was initially charged with 4768 g of a 37.3% by weight sodium acrylate solution which had been filtered through activated carbon beforehand and 595 g of water. With stirring and simultaneous cooling, 612 g of acrylic acid were metered in gradually. After bubbling nitrogen through for 30 minutes, 6.91 g of 3-tuply ethoxylated glyceryl triacrylate and 9.87 g of a 30% by weight solution of sodium persulfate in water were added, and the mixture was stirred for a further minute. In the course of this, the reaction mixture was cooled such that the temperature at no time exceeded 35° C. and was approx. 20° C. toward the end. The reaction mixture was subsequently transferred by means of a pump into an IKA® HKS horizontal kneader (capacity 10 l) which had been preheated to 60° C. and was purged with nitrogen gas. Finally, in the horizontal kneader, 5.92 g of a 1% by weight solution of ascorbic acid in water and 1.97 g of 3% by weight hydrogen peroxide were added with stirring in the horizontal kneader. The reactor jacket temperature was raised to 95° C. and, after 15 minutes of reaction time, the polymer gel formed was removed from the horizontal kneader. The polymer gel thus obtained was distributed on metal sheets with wire bases and dried in a forced air drying cabinet at 165° C. for 90 minutes. This wall followed by comminution with an ultracentrifugal mill, and the product was screened off to 150 to 850 μm. The base polymer thus prepared had a centrifuge retention capacity (CRC) of 36.5 g/g.

Postcrosslinking of the Base Polymer

Example 3

1 kg of the water-absorbent polymer particles prepared in example 1 were preheated in a laboratory oven to 50° C. Upon the water-absorbent polymer particles reached the oven temperature the water-absorbent polymer particles were put into a laboratory ploughshare mixer with a heated jacket (model M 5; manufactured by Gebrüder Lödige Maschinenbau GmbH; Paderborn; Germany). A postcrosslinker solution was prepared by mixing 0.7 g 2-hydroxyethyl-2-oxazolidon, 0.7 g 1,3-propanediole, 9.0 g of propylene glycol, and 5.0 g of deionized water and combined with 30.0 g of aluminium dihydroxy monoacetate solution (20.0% by weight, stabilized with boric acid). At a mixer speed of 450 rpm, the combined solution was added by a disposable syringe to the polymer powder over a two minute time period. The product temperature was raised kept at 180° C. for 60 minutes at a mixer speed of 210 rpm. After cooling down of the mixer, the product was discharged.

The water-absorbent polymer particles had a centrifuge retention capacity (CRC) of 34.0 g/g, a free swell gel bed permeability (GBP) of 62 darcies and a saline flow conductivity (SFC) of $23 \times 10^{-7}$ cm³s/g.

Example 4

Example 3 was repeated, except that the water-absorbent polymer particles prepared in example 1 were replaced by water-absorbent polymer particles prepared in example 2.

The water-absorbent polymer particles had a centrifuge retention capacity (CRC) of 30.9 g/g, a free swell gel bed permeability (GBP) of 106 darcies and a saline flow conductivity (SFC) of $89 \times 10^{-7}$ cm³s/g.

Example 5 (Comparative)

Example 3 was repeated, except that the postcrosslinker solution was replaced by a solution that consists of 0.7 g 2-hydroxyethyl-2-oxazolidon, 0.7 g 1,3-propanediole, and 9.0 g of propylene glycol and the aluminium dihydroxy monoacetate solution was replaced by 100 g of aluminium triacetate solution (5.2% by weight).

The water-absorbent polymer particles had a centrifuge retention capacity (CRC) of 26.7 g/g, a free swell gel bed permeability (GBP) of 62 darcies and a saline flow conductivity (SFC) of $107 \times 10^{-7}$ cm³s/g.

Example 6

Example 3 was repeated, except that the aluminium dihydroxy monoacetate solution was replaced by 30.0 g of aluminium dihydroxy monoacetate solution (20.0% by weight, stabilized with aspartic acid).

The water-absorbent polymer particles had a centrifuge retention capacity (CRC) of 33.7 g/g, a free swell gel bed permeability (GBP) of 33 darcies and a saline flow conductivity (SFC) of $29 \times 10^{-7}$ cm³s/g.

Example 7

Example 3 was repeated, except that the aluminium dihydroxy monoacetate solution was replaced by 30.0 g of aluminium dihydroxy monoacetate solution (20.0% by weight, without stabilizer).

The water-absorbent polymer particles had a centrifuge retention capacity (CRC) of 32.4 g/g, a free swell gel bed permeability (GBP) of 33 darcies and a saline flow conductivity (SFC) of $30 \times 10^{-7}$ cm$^3$s/g.

Example 8

Example 3 was repeated, except that the postcrosslinker solution was replaced by a solution that consists of 0.7 g 2-hydroxyethyl-2-oxazolidon, 0.7 g 1,3-propanediole, 9.0 g of propylene glycol, and 19.6 g of deionized water and the aluminium dihydroxy monoacetate solution was replaced by 15.4 g of aluminium dihydroxy monoacetate solution (20.0% by weight, stabilized with boric acid).

The water-absorbent polymer particles had a centrifuge retention capacity (CRC) of 32.3 g/g, a free swell gel bed permeability (GBP) of 32 darcies and a saline flow conductivity (SFC) of $31 \times 10^{-7}$ cm$^3$s/g.

Example 9

Example 3 was repeated, except that the postcrosslinker solution was replaced by a solution that consists of 0.7 g 2-hydroxyethyl-2-oxazolidon, 0.7 g 1,3-propanediole, and 9.0 g of propylene glycol and the aluminium dihydroxy monoacetate solution was replaced by 46.1 g of aluminium dihydroxy monoacetate solution (20.0% by weight, stabilized with boric acid).

The water-absorbent polymer particles had a centrifuge retention capacity (CRC) of 33.1 g/g, a free swell gel bed permeability (GBP) of 96 darcies and a saline flow conductivity (SFC) of $21 \times 10^{-7}$ cm$^3$s/g.

Example 10

Example 3 was repeated, except that the aluminium dihydroxy monoacetate solution was replaced by 30.0 g of aluminium dihydroxy aminoacetate slurry (25.0% by weight).

The water-absorbent polymer particles had a centrifuge retention capacity (CRC) of 32.8 g/g, a free swell gel bed permeability (GBP) of 40 darcies and a saline flow conductivity (SFC) of $90 \times 10^{-7}$ cm$^3$s/g.

Preparation of the Fluid-Absorbent Cores

Example 11

A first substrate layer was laid on a flat cardboard and covered with a pattern template. The first substrate was a commercially available 15 gsm nonwoven (AVGOL American Inc.; Mocksville; U.S.A.) having a size of 14.5 inch×4.5 inch (36.8 cm×11.4 cm).

The template was a commercially available stainless steel plate having square end slots and an open area of 40% (Direct Metals Company, LLC; Kennesaw; U.S.A.). The template had a size of 10 inch×14 inch (25.4 cm×35.6 cm). The slots had a size of ¼ inch×⅜ inch (0.64 cm×0.95 cm) and were side staggered having end and side bars of 3/16 inch (0.48 cm).

11 g of water-absorbent polymer particles prepared in example 3 were added as evenly as possible onto the template and then evenly distributed with a smooth rubber blade to create a pattern of water-absorbent polymer particles on the first substrate layer.

A piece of a commercially available pressure sensitive adhesive having 20 gsm (BASF Corporation; Monaca; U.S.A.) on a release paper was transferred onto a second substrate layer (corresponding to 0.84 g adhesive). Next, the template on the first substrate layer was carefully removed and the second substrate layer was placed on the top of the first substrate layer with the adhesive side of the second substrate layer facing the top side with the water-absorbent polymer particles of the first substrate layer. The second substrate was a commercially available 15 gsm nonwoven (AVGOL American Inc.; Mocksville; U.S.A.) having a size of 14.5 inch×4.5 inch (36.8 cm×11.4 cm).

The single layered fluid-absorbent core was transferred with the cardboard into a Carver® Press model Auto Series 4425.4DI0A01 (Carver Inc.; Wabash; U.S.A.). The press was pre-set to 10,000 lbs (corresponding to 1,054 kPa) and immediately stopped once the pre-set pressure was reached.

The resulting fluid-absorbent core was analyzed, the results are summarized in table 1.

Examples 13 to 17

Example 11 was repeated, except that the water-absorbent polymer particles prepared in example 3 were replaced by the water-absorbent polymer particles prepared in examples 4 to 9. The resulting fluid-absorbent core was analyzed, the results are summarized in table 1.

Example 18

Example 11 was repeated, except that the pattern template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm). The resulting fluid-absorbent core was analyzed, the results are summarized in table 1.

Examples 19 to 23

Example 18 was repeated, except that the water-absorbent polymer particles prepared in example 3 were replaced by the water-absorbent polymer particles prepared in examples 4 to 8 or in example 10. The resulting fluid-absorbent core was analyzed, the results are summarized in table 1.

Example 24

Example 11 was repeated, except that the first and the second substrate were a 17 gsm forming tissue (Cellu Tissue Holdings, Inc.; East Hartford; U.S.A.) having a size of 14.5 inch×4.5 inch (36.8 cm×11.4 cm). The resulting fluid-absorbent core was analyzed, the results are summarized in table 1.

Examples 25 and 26

Example 24 was repeated, except that the water-absorbent polymer particles prepared in example 3 were replaced by the water-absorbent polymer particles prepared in examples 4 and 5. The resulting fluid-absorbent core was analyzed, the results are summarized in table 1.

TABLE 1

Results of the wet SAP shake out procedure (single layered fluid-absorbent cores)

| Example | water-absorbent polymer particles | substrate | pattern template | SAPLoss |
|---|---|---|---|---|
| Example 11 | Example 3 | nonwoven | square slots | 2.0 wt. % |
| Example 12 | Example 4 | nonwoven | square slots | 7.6 wt. % |
| Example 13 | Example 5*) | nonwoven | square slots | 29.5 wt. % |
| Example 14 | Example 6 | nonwoven | square slots | 6.4 wt. % |
| Example 15 | Example 7 | nonwoven | square slots | 5.9 wt. % |
| Example 16 | Example 8 | nonwoven | square slots | 13.5 wt. % |
| Example 17 | Example 9 | nonwoven | square slots | 5.7 wt. % |
| | ASAP® 531T | nonwoven | square slots | 50.1 wt. % |
| | Hysorb® B7055 | nonwoven | square slots | 47.2 wt. % |
| | Hysorb® T8760 | nonwoven | square slots | 16.8 wt. % |
| Example 18 | Example 3 | nonwoven | round holes | 3.6 wt. % |
| Example 19 | Example 4 | nonwoven | round holes | 2.9 wt. % |
| Example 20 | Example 5*) | nonwoven | round holes | 23.2 wt. % |
| Example 21 | Example 6 | nonwoven | round holes | 6.3 wt. % |
| Example 22 | Example 8 | nonwoven | round holes | 1.9 wt. % |
| Example 23 | Example 10 | nonwoven | round holes | 6.1 wt. % |
| | ASAP® 531T | nonwoven | round holes | 31.3 wt. % |
| | Hysorb® B7055 | nonwoven | round holes | 21.0 wt. % |
| | Hysorb® T8760 | nonwoven | round holes | 13.6 wt. % |
| Example 24 | Example 3 | tissue paper | square slots | 3.4 wt. % |
| Example 25 | Example 4 | tissue paper | square slots | 6.6 wt. % |
| Example 26 | Example 5*) | tissue paper | square slots | 15.1 wt. % |
| | ASAP® 531T | tissue paper | square slots | 65.2 wt. % |
| | Hysorb® B7055 | tissue paper | square slots | 42.1 wt. % |
| | Hysorb® T8760 | tissue paper | square slots | 17.5 wt. % |

ASAP® 531T, Hysorb® B7055, and Hysorb® T8760 are commercially available water-absorbent polymer particles (BASF SE; Ludwigshafen; Germany).

Example 27

A first substrate layer was laid on a flat cardboard and covered with a pattern template. The first substrate was a commercially available 15 gsm nonwoven (AVGOL American Inc.; Mocksville; U.S.A.) having a size of 14.5 inch×4.5 inch (36.8 cm×11.4 cm).

The template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm).

11 g of water-absorbent polymer particles prepared in example 3 were added as evenly as possible onto the template and then evenly distributed with a smooth rubber blade to create a pattern of water-absorbent polymer particles on the first substrate layer.

A piece of a commercially available pressure sensitive adhesive having 20 gsm (BASF Corporation; Monaca; U.S.A.) on a release paper was transferred onto a second substrate layer (corresponding to 0.84 g adhesive). Next, the template on the first substrate layer was carefully removed and the second substrate layer was placed on the top of the first substrate layer with the adhesive side of the second substrate layer facing the top side with the water-absorbent polymer particles of the first substrate layer. The second substrate was a commercially available 15 gsm nonwoven (AVGOL American Inc.; Mocksville; U.S.A.) having a size of 14.5 inch×4.5 inch (36.8 cm×11.4 cm).

The second substrate layer wa covered with the pattern template and further 11 g of water-absorbent polymer particles prepared in example 3 were added as evenly as possible onto the template and then evenly distributed with a smooth rubber blade to create a pattern of water-absorbent polymer particles on the second substrate layer.

A piece of a commercially available pressure sensitive adhesive having 20 gsm (BASF Corporation; Monaca; U.S.A.) on a release paper was transferred onto a third substrate layer (corresponding to 0.84 g adhesive). Next, the template on the second substrate layer was carefully removed and the third substrate layer was placed on the top of the second substrate layer with the adhesive side of the third substrate layer facing the top side with the water-absorbent polymer particles of the second substrate layer. The third substrate was a 17 gsm forming tissue (Cellu Tissue Holdings, Inc.; East Hartford; U.S.A.) having a size of 14.5 inch×4.5 inch (36.8 cm×11.4 cm).

The multi layered fluid-absorbent core was transferred with the cardboard into a Carver® Press model Auto Series 4425.4DI0A01 (Carver Inc.; Wabash; U.S.A.). The press was pre-set to 10,000 lbs (corresponding to 1,054 kPa) and immediately stopped once the pre-set pressure was reached.

The resulting fluid-absorbent core was analyzed, the results are summarized in table 2.

Examples 28 and 29

Example 27 was repeated, except that the water-absorbent polymer particles prepared in example 3 were replaced by the water-absorbent polymer particles prepared in examples 4 and 5. The resulting fluid-absorbent core was analyzed, the results are summarized in table 2.

Example 30

Example 27 was repeated, except that the second substrate was a 17 gsm forming tissue (Cellu Tissue Holdings, Inc.; East Hartford; U.S.A.) having a size of 14.5 inch×4.5 inch (36.8 cm×11.4 cm). The resulting fluid-absorbent core was analyzed, the results are summarized in table 2.

Examples 31 and 32

Example 30 was repeated, except that the water-absorbent polymer particles prepared in example 3 were replaced by the water-absorbent polymer particles prepared in examples 4 and 5. The resulting fluid-absorbent core was analyzed, the results are summarized in table 2.

TABLE 2

Results of the wet SAP shake out procedure
(multi layered fluid-absorbent cores)

| Example | water-absorbent polymer particles | second substrate | SAPLoss |
|---|---|---|---|
| Example 27 | Example 3 | nonwoven | 4.2 wt. % |
| Example 28 | Example 4 | nonwoven | 2.7 wt. % |
| Example 29 | Example 5*) | nonwoven | 15.6 wt. % |
| Example 30 | Example 3 | tissue paper | 4.1 wt. % |
| Example 31 | Example 4 | tissue paper | 6.1 wt. % |
| Example 32 | Example 5*) | tissue paper | 13.1 wt. % |

*)comparative

The invention claimed is:

1. A fluid-absorbent core comprising a substrate layer, at least 75% by weight of water-absorbent polymer particles, and an adhesive, wherein the water-absorbent polymer particles comprise a basic salt of a polyvalent metal cation and a monovalent carboxylic acid anion on a surface and the wet SAP shake out of water-absorbent polymer particles out of the fluid-absorbent core is less than 10% by weight.

2. The fluid-absorbent core according to claim 1, wherein the fluid-absorbent core comprises at least 85% by weight of the water-absorbent polymer particles.

3. The fluid-absorbent core according to claim 1, wherein the fluid-absorbent core comprises not more than 10% by weight of the adhesive.

4. The fluid-absorbent core according to claim 1, wherein the wet SAP shake out of water-absorbent polymer particles out of the fluid-absorbent core is less than 5% by weight.

5. The fluid-absorbent core according to claim 1, wherein the adhesive is a pressure sensitive adhesive.

6. The fluid-absorbent core according to claim 1, wherein the substrate layer is a nonwoven layer or a tissue paper.

7. The fluid-absorbent core according to claim 1, wherein the fluid-absorbent core comprises at least two layers of water-absorbent polymer particles.

8. The fluid-absorbent core according to claim 1, wherein the water-absorbent polymer particles are placed in discrete regions.

9. The fluid-absorbent core according to claim 1, wherein the water-absorbent polymer particles comprise from 0.001 to 0.05 mol of the polyvalent metal cation per 100 g of the water-absorbent polymer particles.

10. The fluid-absorbent core according to claim 1, wherein the polyvalent metal cation is a trivalent metal cation.

11. The fluid-absorbent core according to claim 1, wherein the monovalent carboxylic acid anion is a substituted or unsubstituted acetic acid anion.

12. The fluid-absorbent core according to claim 1, wherein the basic salt comprises at least one stabilizer.

13. The fluid-absorbent core according to claim 12, wherein the stabilizer is boric acid and/or aspartic acid.

14. The fluid-absorbent core according to claim 1, wherein the water-absorbent polymer particles have a centrifuge retention capacity of at least 20 g/g and a free swell gel bed permeability of at least 20 Darcies and/or a saline flow conductivity of at least $30 \times 10^{-7}$ cm$^3$s/g.

15. The fluid-absorbent article, comprising
(A) an upper liquid-pervious layer,
(B) a lower liquid-impervious layer and
(C) a fluid-absorbent core according to claim 1 between the layer (A) and the layer (B),
(D) an optional acquisition-distribution layer between (A) and (C),
(E) an optional tissue layer disposed immediately above and/or below (C); and
(F) other optional components.

* * * * *